Sept. 10, 1963 H. C. SWIM ETAL Plant Pat. 2,282
ROSE PLANT
Filed Aug. 28, 1962
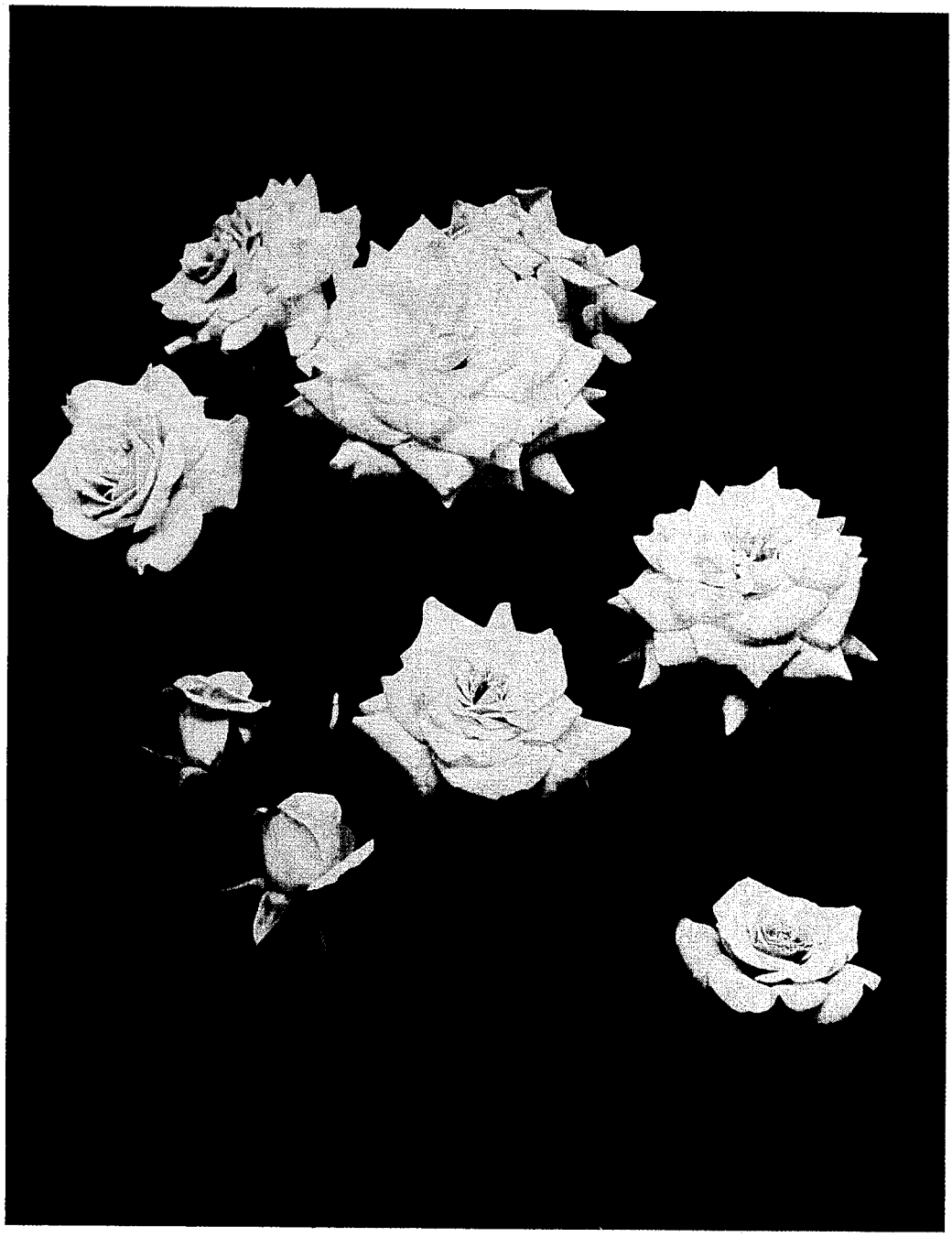
Inventors.
H. C. Swim and
O. L. Weeks
By: Robb & Robb
attorneys.

United States Patent Office

Plant Pat. 2,282
Patented Sept. 10, 1963

2,282
ROSE PLANT

Herbert C. Swim, 1329 College Way, Ontario, Calif., and O. L. Weeks, Chino, Calif.

Filed Aug. 28, 1962, Ser. No. 220,110
1 Claim. (Cl. Plt.—26)

The present invention relates to a new and distinct variety of rose plant of the hybrid polyantha (floribunda) class, which was originated by us by crossing the variety "Spartan" (Plant Patent No. 1,357) with the variety "Garnette" (unpatented).

As the result of this breeding, we have produced a new rose variety which is endowed with the following unique combination of characteristics which are outstanding therein and which distinguish it from its parents, as well as from all other varieties of which we are aware:

(1) A vigorous habit of plant growth when grown in the greenhouse, and as demonstrated by an early initiation of each new growth cycle;

(2) Dark green foliage of heavy and leathery texture;

(3) Relatively longer and straighter flower stems than most varieties of the floribunda class;

(4) Relative freedom from prickles on the branches and particularly on the flower stems;

(5) Abundant production of flowers when grown in the greenhouse for cut flowers, as demonstrated by often having 20 or more flowers per plant in one crop;

(6) A high-centered form of the opening flowers, causing the flowers to retain the form of the original buds until the opening process is completed in the center portion of the flowers;

(7) An imbricated-concentric flower petal pattern occurring during the opening process of the flowers, and a star-pointed effect of the open blooms resulting from folding downward of the lateral outer petal margins; and (8) An attractive and distinctive dainty light pink general color tonality of the flowers.

In comparison with its seed parent, "Spartan," the flower buds are from long-pointed to urn-shaped, instead of the short-pointed to ovoid shape of the parent flower buds; the new variety has from 32 to 50 or more petals per flower, as compared with the average of 30 petals in the parent variety; the new variety has the lateral margins of the outer flower petals folded downward, leaving the apices acutely pointed and giving the open flowers a star-pointed effect, whereas the outer petals of the parent variety remain relatively flat throughout the life of the flowers; and the general color tonality of the flowers of the new variety is light pink in contrast to the flower color of the parent variety which ranges from orange-red to reddish coral.

As compared with its pollen parent, "Garnette," the branches of the new variety are relatively straight instead of the characteristic zig-zag from node to node like the branches and stems of this parent; the new variety has substantially longer stems; the nodes (leaf axils) are substantially farther apart; the outer flower petals of the new variety are folded downward along the lateral margins in such a way as to give the open flowers a star-pointed effect, instead of being relatively flat as in the parent variety; and the flowers of the new variety are light pink in color instead of the usual garnet-red color of the parent variety.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; greenhouse; seedling; for cut flowers.
Class: Hybrid polyantha (floribunda).
Breeding: Seedling.
*Seed parent.*—"Spartan."
*Pollen parent.*—"Garnette."
Propagation: Holds its distinguishing characteristics through succeeding propagations by budding.

*Flower*

Locality where grown and observed: Chino, California.
Flowers borne: Singly, and from 2 to 4, and occasionally more, to stem in more or less flat cluster; on long stems for its class, with the stems having normal strength.
Quantity of bloom: Abundant, in greenhouse.
Continuity: Continuous.
Fragrance: Slight. Nature—tea.
Bud:

*Peduncle.*—From short to medium length; medium caliper; erect; with numerous small gland-tipped cilia. Color—medium yellowish green.

*Before calyx breaks.*—Size—medium for its class. Form—pointed; with a conspicuous neck (incipient seed pod), with foliaceous appendages on the surface of the bud; often with slender foliaceous parts extending beyond the tip of the bud equal to from ¼ to ½ or more of its length. Color—varying from Pale Orange Yellow, Plate 7.5YR 9/4 to Moderate Yellowish Pink, Plate 10R 8/6.

*As calyx breaks.*—Color—varying with weather and feeding practices from Light Yellowish pink, Plate 2.5YR 9/3, or lighter, to Moderate Yellowish Pink, Plate 7.5R 8/6.

*As first petal opens.*—Size—medium for its class. Form—long; from pointed to urn-shaped. Color: outside—varying with weather and feeding practices from Light Yellowish Pink, Plate 2.5YR 9/3, or lighter, to Moderate Yellowish Pink, Plate 7.5R 8/6; inside—varying with weather and feeding practices from Light Yellowish Pink, Plate 2.5YR 9/3 at outer edges, with heart of bud Light Yellowish Pink, Plate 7.5R 9/3; to Light Yellowish Pink, Plate 7.5R 9/3 at outer edges with heart of bud Moderate Yellowish Pink, Plate 7.5R 8/6.

*Opening.*—Opens up well.

Bloom:

*Size (when fully open).*—From medium to large for its class; from 2½ inches to 3 inches.

*Petalage.*—From double to very double; from 32 to 50 or more petals; arranged regularly.

*Form.*—High centered at first, becoming from open to high centered at maturity; petals being at first arranged in rather tightly imbricated-concentric pattern with lateral margins folded down slightly, giving impression of points to the petals, later becoming more loosely imbricated at maturity, with folding downward of margins and pointing of apex becoming more acute on outer petals and progressively less acute toward the center of the flower.

Petals:

*Texture.*—Thick; leathery. Inside—satiny. Outside—satiny.

*Shape.*—Outside—Broadly obovate with apex short acute. Intermediate—obovate, with apex rounded. Inside—obovate-truncate, with apex rounded and with margins often faintly crinkled.

This description of a newly opened flower was made from a rose grown in a greenhouse in the month of July in Chino, California:

*Color* (May be modified by being dotted and blotched with crimson just before petals drop and after original colors have faded.)—Outer petal: outside surface—near Pale Purplish Pink, Plate 7.5RP 9/2, except for midrib which from base to center of petal is near Brilliant Yellow Green, Plate 2.5GY 9/8; inside surface—near pale Purplish Pink, Plate 7.5RP 9/2, except for midrib which from base to center of petal is near Brilliant Yellow Green, Plate 5GY 8/8. Intermediate petal: outside surface—between Pale Purplish Pink, Plate 2.5RP 9/2, and Light Yellowish Pink, Plate 7.5R 9/3, except somewhat more muted than the latter color, with faint greenish yellow influence about midrib from base to center of petal; inside surface—between Light Yellowish Pink, Plate 2.5YR 9/3, and Light Yellowish Pink, Plate 7.5R 9/3, with small area about base slightly modified by faint greenish yellow coloration. Inner petal: outside surface—between Light Yellowish Pink, Plate 7.5R 9/3 and Pale Pink, Plate 2.5R 9/3, except for midrib which is a pale greenish yellow at base but sometimes changes quickly to a faint crimson line extending to apex, particularly on petaloids; most petals are uniform except for basal modification of greenish yellow; inside surface—near Light Yellowish Pink, Plate 7.5R 9/3, except for small area at base which has a faint greenish yellow cast.

This description of a rose that was open for three days in a greenhouse was made during the month of July at Chino, California:

*Color* (May be modified by being dotted and blotched with crimson just before petals drop and after original colors have faded.)—outer petal: outside surface—near white, except with faint greenish yellow influence near base; inside surface—near white, except for faint greenish yellow influence near base. Inner petal: outside surface—near Pale Purplish Pink, Plate 2.5RP 9/2, except for small area about base influenced by a faint greenish yellow color; inside surface—between White and Pale Purplish Pink, Plate 2.5RP 9/2, except for small area about base which is modified by a faint greenish yellow color.

*General color effect.*—Newly opened flower—outer edges of flower are between Light Yellowish Pink, Plate 2.5YR 9/3 and Light Yellowish Pink, Plate 7.5R 9/3, with heart of flower between Moderate Yellowish Pink, Plate 10R 8/6 and Moderate Yellowish Pink, Plate 7.5R 8/6; color differentiation between outer and inner portions of flower is largely lost when last petals unfold and spread open, due apparently to some build-up of color by reflection of the outer surfaces, intensified by shadow to the inner surfaces adjacent thereto. Three days open—from near Pale Purplish Pink, Plate 7.5R 9/2 to Light Purplish Pink, Plate 7.5R 9/3.

*Behavior.*—Persist somewhat beyond attractive stage.

*Flower longevity.*—Cut roses grown in greenhouse and kept at living-room temperatures—6 days during July.

*Reproductive Organs*

Stamens: Medium quality; arranged somewhat irregularly about pistils; a few petaloids occasionally intermixed.

Filaments: Medium length; most with anthers. Color—white.

Anthers: Small; open at various times. Color—reddish yellow.

Pollen: Moderate quantity. Color—gold.

Pistils: Medium number.

Styles: Uneven; medium length; thin; loosely bunched.

Stigma: Color—white.

Ovaries: Most protruding from calyx, but a few enclosed.

Hips: None observed.

Sepals: Permanent; moderately long; some recurved.

Seeds: None observed.

*Plant*

Foliage:

*Leaves.*—Compound 3–5 leaflets; normal abundance; moderately large; moderately heavy and leathery.

*Leaflets.*—Shape—ovoid, with apex acute. Base—rounded usually, but sometimes asymmetrical. Margin—both singly and doubly serrate.

*Color.*—Mature: upper surface—very dark green; under surface—normal grey-green. Young: upper surface—dark red; undersurface—dark red.

*Rachis (the supporting stem of the compound leaf).*—From light to medium in weight and caliper. Upper side—grooved; ridges have from several to many stipitate glands. Under side—smooth, except for occasional prickle.

*Stipules.*—From short to medium length; medium width; with points of medium length turning out at an angle of less than 45°.

*Disease resistance.*—From medium to good resistance to powdery mildew, as compared with common commercial varieties grown under comparable greenhouse conditions at Chino, California.

Growth:

*Habit.*—Bushy; upright; much-branched.

*Growth.*—Very vigorous in the greenhouse.

*Canes.*—Medium caliper.

*Main stems.*—Color—green. Large prickles—few; from medium length to long; straight; with short, oval base; color—brown. Small prickles—none. Hairs—none.

*Branches.*—Color—green. Large prickles—sometimes few, but often none; medium length; straight; with short, oval base; color—brown. Small prickles—none. Hairs—none.

*New shoots.*—Color—green, mostly overlaid with red. Large prickles—from very few to none; medium length; straight; with short, oval base; color—red at base, with yellowish green tip. Small prickles—none. Hairs—none.

We claim:

A new and distinct variety of rose plant of the hybrid polyantha (floribunda) class, substantially as herein shown and described, characterized particularly as to novelty by the unique combination of a vigorous habit of plant growth when grown in the greenhouse, with early initiation of each new growth cycle, dark green foliage of heavy and leathery texture, relatively long and straight flower stems, relative freedom from prickles on the branches and particularly on the flower stems, prolific greenhouse production for cut flowers, a high-centered form of the original buds until the opening process is completed in the center portion of the flowers, an imbricated-concentric flower petal pattern in the opening flowers, changing to a star-pointed effect of the open flowers attributed to folding downward of the lateral margins of the outer flower petals, and a distinctive and attractive dainty light pink general color tonality of the flowers.

No references cited.